United States Patent
Timmermans et al.

(10) Patent No.: US 6,512,156 B1
(45) Date of Patent: Jan. 28, 2003

(54) METHOD AND APPARATUS FOR CONTROLLING SEVERITY OF CRACKING OPERATIONS BY NEAR INFRARED ANALYSIS IN THE GAS PHASE USING FIBER OPTICS

(75) Inventors: Gerardus J. Timmermans, Terneuzen (NL); Henrious J. Morgenstern, Terneuzen (NL)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 08/734,945

(22) Filed: Oct. 22, 1996

(51) Int. Cl.$^7$ ................................................ C10G 9/16
(52) U.S. Cl. ................... 585/501; 585/401; 585/701; 208/106; 208/130; 208/131; 208/132; 208/DIG. 1; 356/319; 356/326; 364/498; 364/500
(58) Field of Search ................. 208/106, 113, 208/DIG. 1, 130, 131, 132; 585/501, 401, 701; 364/498, 500; 356/319, 326

(56) References Cited

U.S. PATENT DOCUMENTS

| | | |
|---|---|---|
| 3,628,028 A | 12/1971 | Thorshelm |
| 3,861,198 A | 1/1975 | Shea |
| 4,172,428 A | 10/1979 | Pariset |
| 4,329,150 A | 5/1982 | Drinkard |
| 4,880,748 A * | 11/1989 | Altman et al. ................ 436/60 |
| 5,082,985 A | 1/1992 | Crouzet et al. ............. 585/501 |
| 5,262,961 A | 11/1993 | Farone ....................... 364/500 |
| 5,348,645 A | 9/1994 | Maggard et al. ............ 208/209 |
| 5,370,790 A * | 12/1994 | Maggard et al. ............ 208/142 |
| 5,412,465 A | 5/1995 | Baylor et al. ................ 356/301 |
| 5,412,581 A | 5/1995 | Tackett ....................... 364/498 |
| 5,446,681 A | 8/1995 | Gethner et al. ............. 364/554 |
| 5,452,232 A | 9/1995 | Espinosa et al. |
| 5,475,612 A | 12/1995 | Espinosa et al. ............ 364/500 |

OTHER PUBLICATIONS

B. M. Wise and B. R. Kowalski, Process chemometrics, *Process Analytical Chemistry*, Blackie Academic & Professional, 1995, pp. 259–312.
A. Espinosa et al., Use NIR technology to optimize plant operations, *Hydrocarbon Processing*, Feb. 1995, pp. 86–92.
Model El–10 Carbon Monoxide Analyzer, AMETEK, Inc., 1990.

* cited by examiner

*Primary Examiner*—Bekir L. Yildirim

(57) ABSTRACT

A two-step method and apparatus for controlling cracking severity in the effluent from a cracking furnace such as an ethylene cracker. The method includes two steps. The first step consists of determining the near infrared spectrum of effluent in-line. The second step consists of changing the temperature and/or residence time of the furnace according to the determination of the first step. The apparatus includes a light source mounted on a conduit for the effluent, a light detector mounted on the opposite side of the conduit from the light source to receive light emitted from the light source, means for sheltering the light source from the effluent, means for sheltering the lights detector from the effluent, means for flowing a fluid past the light source at a higher pressure than the pressure of the effluent; and means for flowing a fluid past the light detector at a higher pressure than the pressure of the effluent.

4 Claims, 4 Drawing Sheets

METHOD AND APPARATUS FOR CONTROLLING SEVERITY OF CRACKING OPERATIONS BY NEAR INFRARED ANALYSIS IN THE GAS PHASE USING FIBER OPTICS

BACKGROUND OF THE INVENTION

Cracking severity is an important parameter for use in determining the optimum operating conditions for cracking furnaces. In a cracking system, a feed mixture is fed to a cracking furnace, which contains at least one cracking tube. The cracking tube is heated to high temperatures, so that the feed mixture decomposes into various constituents. The constituents together are known as crack gas or effluent. Cracking severity, which is the extent to which the feed mixture is broken down, is controlled by altering the temperature of the cracking furnace, altering the residence time of the feed and constituents inside the cracking tubes, or changing the steam dilution in the case of steam cracking, in order to optimize the composition of the effluent.

The tubes in a cracking furnace are typically very hot, around 1000 degrees centigrade and higher, depending on the location within the furnace. Usually, the crack gas is cooled after exiting the furnace. However, the crack gas is still hot after cooling, at around 350 degrees centigrade and higher. Deposition of materials such as carbon usually occurs on the tubes and process lines at such high temperatures, a problem known as "coking", or "coke deposition". Coking has interfered with the ability to accurately measure the concentration of the constituents within the tubes and process lines, because the sample lines or sampling systems for instruments used online often become dirty and plug as a result of coking.

The coking problem has greatly hampered the reliable analysis of the cracking gas, thus preventing improved process control based on cracking severity. Cracking furnace operators have tried to develop different methods in order to control cracking severity. Often, a portion of the effluent of the cracking process is brought outside of the cracking process lines in order to analyze the composition of the effluent. Such a procedure sometimes requires heating of the sampled effluent line to prevent condensation of the heavies or tars before the transport of the non-condensed part of the effluent to the analyzer, because the heavies can cause plugging. Another procedure might consist of condensing the effluent and removing the heavies before the effluent is transported to the analyzer. These procedures generally employ gas chromatograph, mass spectroscopy, or a combination of gas chromatograph and mass spectroscopy to analyze the effluent. However, the resulting measurement can be unreliable, because a troublesome sampling system and removal of heavies can result in plugging problems.

Another procedure commonly used for determining effluent composition is to predict the effluent composition from the composition of the feed stream. This determination typically begins with an off-line analysis of the feed stream composition in the laboratory using near infrared (NIR) analysis. The NIR analysis is then used to predict the composition of the effluent based on a mathematical model. See, for example, U.S. Pat. No. 5,452,232, U.S. Pat. No. 5,082,985, and U.S. Pat. No. 5,475,612. However, the accuracy of the prediction of the effluent composition using this procedure depends on the model used. Numerous parameters, such as the type and condition of the furnace, temperature, pressure, steam dilution, and coke deposition, must be taken into account in order for the model to be sufficiently precise. Furthermore, if the composition of the feed stream changes, a new model must usually be developed. Therefore, such mathematical models are often inaccurate and insufficiently reliable for controlling cracking severity.

The above-described procedures for measuring the composition of the feed stream on the inlet of the cracking furnace typically employ spectrometric methods, such as NIR, to analyze the particular stream of interest. The advantages of spectrometric methods are that no sample handling is required, and such measurements can occur essentially instantaneously. However, spectroscopic methods have not been performed directly on the outlet of the cracking furnace tubes, due to the above described coking problems.

It would be an advance in the art of cracking severity control if a method could be developed for analyzing furnace effluent directly in the outlet of the cracking furnace tubes, thereby eliminating sample handling concerns and avoiding the need for a mathematical model. The resulting measurement would be direct, reliable, precise, and nearly instantaneous.

SUMMARY OF THE INVENTION

The instant invention solves the above mentioned problem of unreliable cracking severity control to a large degree. The instant invention provides for direct online analysis of cracking furnace effluent, without any sampling requirements.

In one aspect, the instant invention is a method for controlling cracking severity in a cracking furnace, the cracking furnace having at least one cracking tube, the cracking tube being heated to a temperature, the cracking tube containing a feed mixture that is fed into the cracking tube and an effluent that flows from the cracking tube, the feed mixture having a residence time in the cracking tube, the method comprising two steps. The first step consists of determining the near infrared spectrum of the effluent in-line. The second step consists of changing a process variable selected from the group consisting of the temperature of the cracking tube and the residence time of the feed mixture in the cracking tube according to the determination of the first step. The feed mixture can also contain a percentage of steam and when it does, then the process variable can be selected from the group consisting of the temperature of the cracking tube, the residence time of the feed mixture in the cracking tube and the percentage of steam in the feed mixture. Preferably, the near infrared spectrum is obtained by shining a beam of near infrared light first through a protective gas-stream, then through the effluent and then through a second protective gas stream to a near infrared spectrometer. A chemometric treatment is preferably made of the determination of the first step to better control the cracking severity.

In a second aspect, the instant invention is an apparatus for analyzing an effluent in-line, comprising a light source mounted on a conduit for the effluent, a light detector mounted on the opposite side of the conduit from the light source to receive light emitted from the light source, means for sheltering the light source from the effluent, means for sheltering the light detector from the effluent, means for flowing a fluid past the Right source at a higher pressure than the pressure of the effluent; and means for flowing a fluid past the light detector at a higher pressure than the pressure of the effluent.

DETAILED DESCRIPTION OF THE INVENTION

Figure 1:
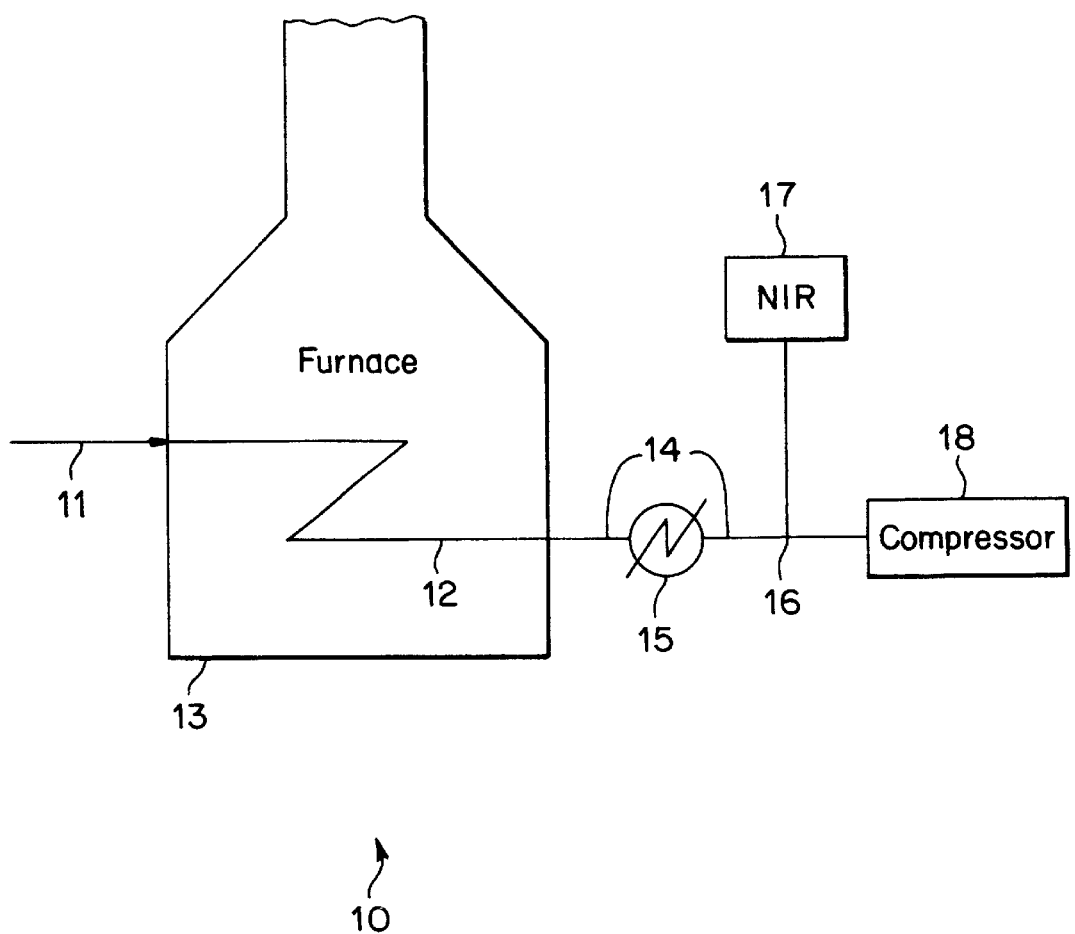
FIG. 1 is a schematic overview of a cracking system.

Referring now to FIG. 1, therein is shown an overview of a cracking system 10 and the location of the instant invention within such a cracking system 10. A feed mixture 11 is fed to a cracking furnace 13, which contains at least one cracking tube 12, where the feed mixture 11 is broken down to form an effluent stream 14.

The feed mixture 11 contains a compound that is to be broken down into smaller constituent parts. For example, naptha is a typical starting material which is broken down to form ethylene, propylene, and various other compounds.

The inside of the cracking furnace 13 is fired, so that the internal cracking tube 12 can be very hot, around 1000 degrees centigrade inside the cracking furnace 13, although the temperature can be higher or lower. A heat exchanger 15 is preferably placed at the outlet of the cracking furnace 13 so that the effluent 14 is cooled to about 350 degrees centigrade, although the effluent can be cooled to any other desired temperature. The effluent can be further treated with a compressor 18. The instant invention can be employed online at point 16.

The extent to which the feed mixture 11 is broken down is commonly known as "cracking severity". In the method aspect of the instant invention, cracking severity is controlled by altering the temperature of the cracking tube, by altering the residence time of the mixture 11 inside the cracking tube 12, or, in the case of steam cracking, by changing the steam dilution, until the composition of the effluent 14 is optimized. The term "residence time" refers to the amount of time the feed mixture is inside the cracking tube 12. The residence time can be altered by adjusting the flow rate of the feed mixture 11. The term "steam dilution" refers to the portion of the feed mixture 11 that is steam.

During the cracking process, coke deposition, or "coking", occurs on the inside of the cracking tube 12. "Coke" is the term used to describe the carbonaceous residue left in the cracking tube 12 and the pipelines carrying the effluent 14 after volatile compounds have passed through the tube. Coke usually interferes with online analysis in cracking operations. Thus, in order to effectively measure the effluent 14 online, the apparatus employed must be designed to cope with these coking problems.

In order to control cracking severity, the instant invention can be employed in-line, at point 16. The term "in-line" is defined herein and in the claims to mean that the instant invention is applied directly to the effluent 14 as the effluent moves through the pipeline in the cracking system 10. No sampling or material handling is required, since the invention is used directly in-line. Point 16 is preferably farther away from the furnace than the heat exchanger 15, so that the effluent is preferably below about 430 degrees centigrade, rather than, for example, 1000 degrees centigrade, which can be the temperature inside the cracking tube 12. However, it should be understood that point 16 can be positioned before the heat exchanger 15, or point 16 can be positioned closer to the compressor 18.

The instant invention utilizes a near infrared analyzer 17 to measure the composition of the effluent 14. The cracking process can be controlled according to the near infrared results by altering the furnace temperature, the residence time, or the steam dilution.

Figure 2:
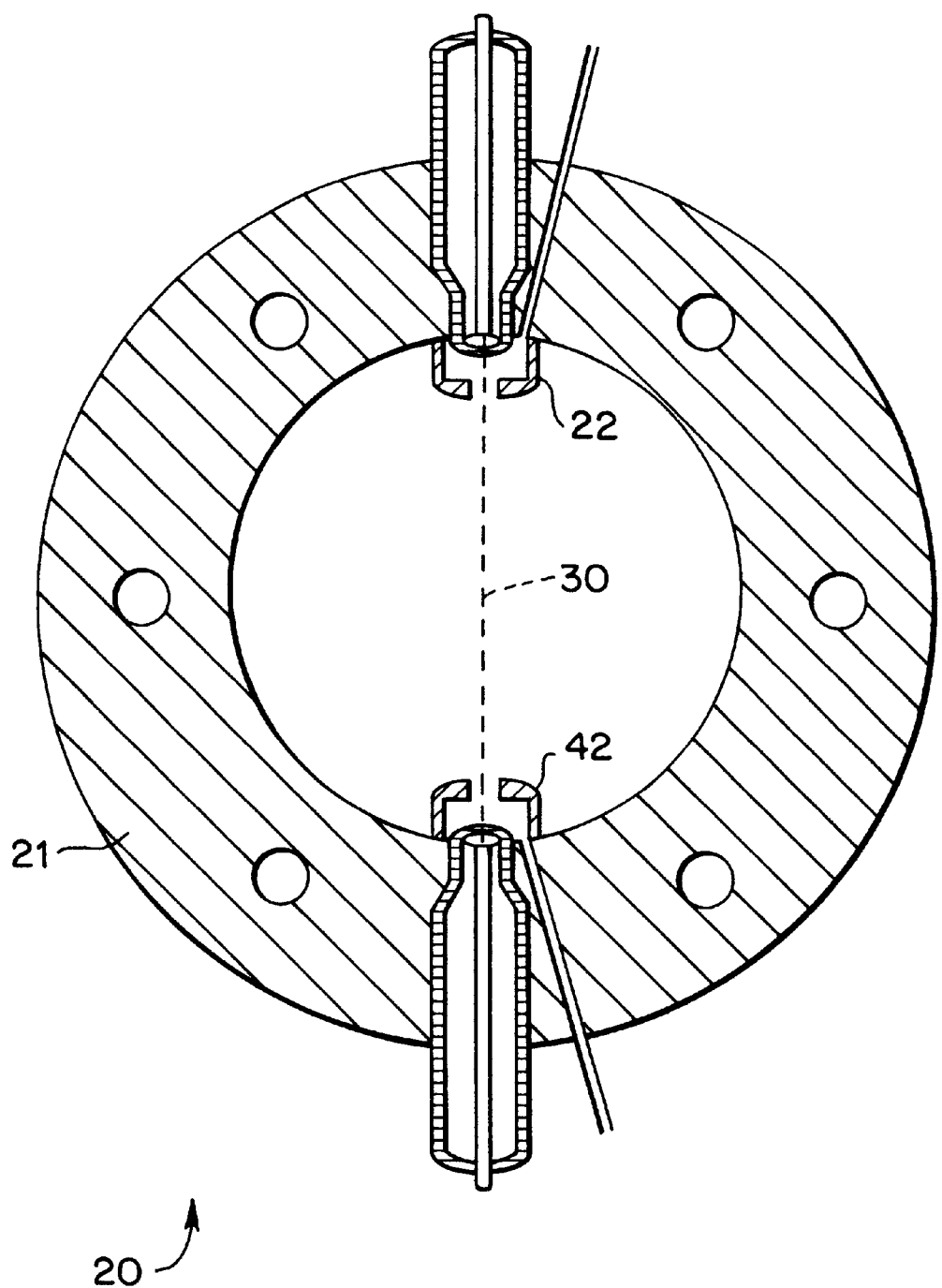
FIG. 2 is a cross-section of an embodiment of an apparatus that can-be used to practice the instant invention.

Referring now to FIG. 2, therein is shown an embodiment of an apparatus 20 that can be used to practice the instant invention. As shown, the apparatus 20 comprises a flange 21, the flange 21 having two bodies, which in this case are caps 22 and 42, positioned directly across from each other along the internal circumference of the flange 21. The space inside the caps 22 and 42 forms internal chambers, or pockets, within the caps 22 and 42.

Figure 2A:
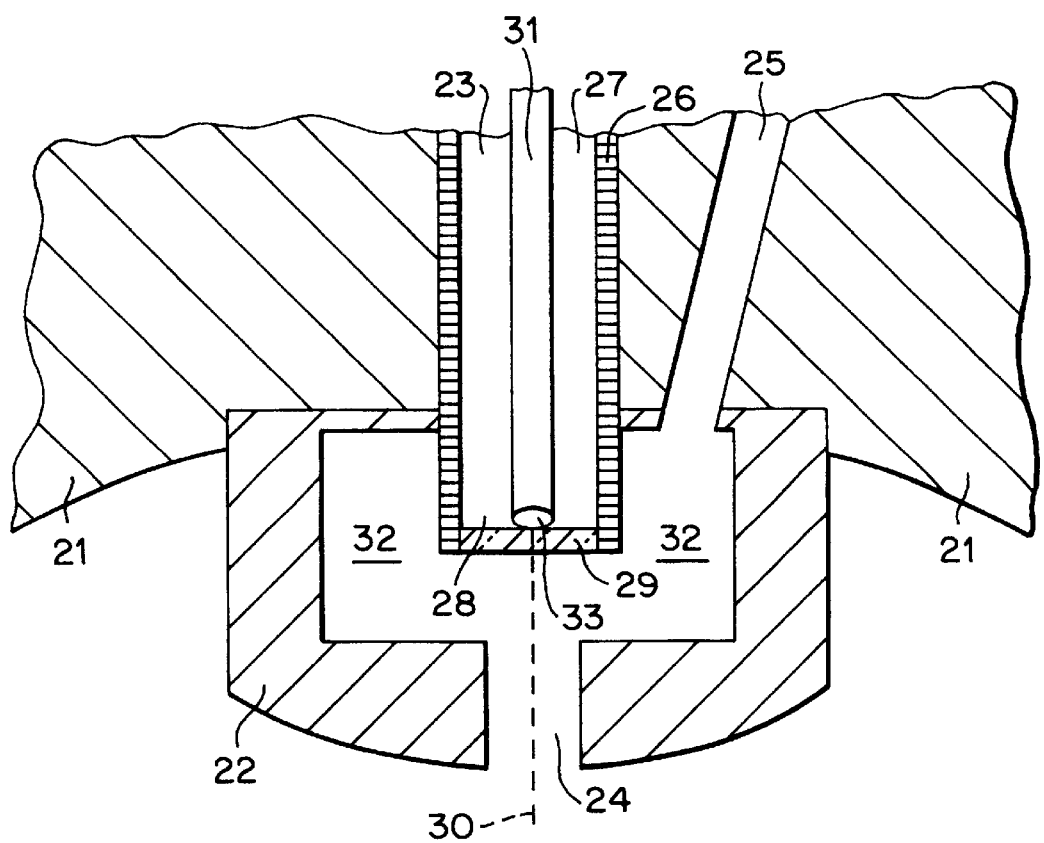
FIG. 2A is a more detailed view of a portion of FIG. 2.

Referring now to FIG. 2A, therein is shown a more detailed view of a cap 22 and the chamber inside the cap 22. As shown, cap 42 has the identical configuration as cap 22, except that cap 42 is on the opposite side of flange 21. The cap 22 preferably has holes 23, 24 and 25 drilled therein. The holes 23, 24 and 25 allow materials to travel to and from the outside of the chamber within the cap 22. As shown, in FIG. 2, cap 42 has an identical configuration that preferably includes three passageways.

Preferably, an optical well 26 is placed through one of the holes 23 and into the chamber within the cap 22. The term "optical well" is used herein to mean a holder for optical measuring equipment, such as optical fibers and/or optical probes. Preferably, the optical well 26 is hollow and a cavity 27 is present inside the optical well 26. The internal end of the optical well has an aperture 28, wherein a window 29 is sealed.

The window 29 can be any useful material which allows light 30 to pass through and can withstand process conditions. Examples of window materials are diamond and sapphire.

The window 29 can be sealed in the aperture 28 in a number of ways. For example, the window can be shaped like a stop-cock, and the aperture can have a tapered configuration, so that the stop-cock window fits into the aperture. Alternatively, the window can be brazed with gold, gold alloy, or any other suitable brazing material.

The optical well 26, together with the window 29 are an example of means for sheltering the source of the light 30, the detector of the light 30, and the other associated optical equipment from the harsh conditions in the effluent line. However, caps 22 can also act as means for sheltering the optical equipment from the severe process conditions.

It is important to note that under severe temperatures such as those in a cracking system, the coefficients of thermal expansion must be considered for the various materials that are used to make the embodiment of the present invention. At a given temperature, differences in thermal expansion coefficients will cause one material to expand to a large degree while another material may only expand to a very small degree. This can create problems such as stretching of the optical fibers, causing potential breakage.

An optical probe 31 is positioned inside the cavity in the optical well 26. The probe 31 preferably comprises optical fibers and a lens 33. The optical fibers can be located inside a ceramic inner holder, which is adapted to fit inside the optical well. The use of the ceramic inner holder avoids stretching the optical fiber due to differences in coefficients of thermal expansion for the fiber and holder materials. The inner holder is preferably spring-loaded, to ensure positioning of the fiber in the focus point of the lens 33. However, other methods for positioning the fibers can be used. The lens 33 in the probe can be any type of optical lens that is suitable for the particular process conditions.

Hole 24 allows light 30 to travel to or from the optical well 26. The window 29 allows light 30 traveling through the hole 24 to enter or exit the cavity inside the optical well 26. The light 30 can be ultraviolet, visible, near infrared, or mid infrared light. Preferably, the light 30 is near infrared light. Near infrared spectroscopy provides nearly instantaneous. measurement of the effluent 14, so that the process conditions can be altered in response to the near infrared analysis. Process conditions include furnace temperature, residence time, and steam dilution. Near infrared analysis is described in greater detail below, in reference to FIG. 3.

A probe identical to probe 31 is preferably placed in the optical well inside cap 42, shown in FIG. 2 on the opposite side of the flange 21 from cap 22. Thus, in the preferred embodiment, the first probe 31 can be a transmission probe, while the opposite probe positioned inside cap 42 can be a detector probe. In an alternative embodiment, instead of a probe, cap 42 can contain a mirror, in which case the probe 31 transmits light 30 and also detects the light reflected from the mirror.

Referring again to FIG. 2A, hole 25 enables a supply of a flowing gas 32 to enter the chamber. A protective layer of gas 32 surrounds the optical well 26, thus protecting the optical well 26 from fouling due to coke-deposition from exposure to the high temperatures in the process line. The gas 32 then flows out of the chamber and into the process by way of the second passageway 24. Preferably, the gas 32 is nitrogen or steam although the gas can be any gas that is inert (i.e., does not react when exposed to the process).

It should be understood that FIG. 2A represents just one of numerous possible embodiments. For example, another equivalent embodiment might have only two holes drilled in a cap. In this alternative, both the optical well and the supply of flowing gas would enter the cap through a single hole. The gas would flow around the optical well and into the crack gas. This embodiment would require fewer holes to be drilled in the flange and the cap. In another embodiment, holes can be drilled directly in the effluent conduit. The NIR source and detector would then be recessed such that they were sheltered from the effluent. The supply of flowing gas would then flow past the NIR source and the NIR detector and through the holes drilled in the conduit.

Preferably, the process is analyzed using near infrared (NIR) analysis. The NIR region of the electromagnetic spectrum is between about 780 and 2500 nanometers. The advantages of NIR spectroscopy include the ability to quickly analyze a process stream, and efficient transmission through readily available optical fibers, allowing remote interfacing of the process with the instrument. Also, NIR spectra show a relatively high signal to noise sensitivity.

Figure 3:
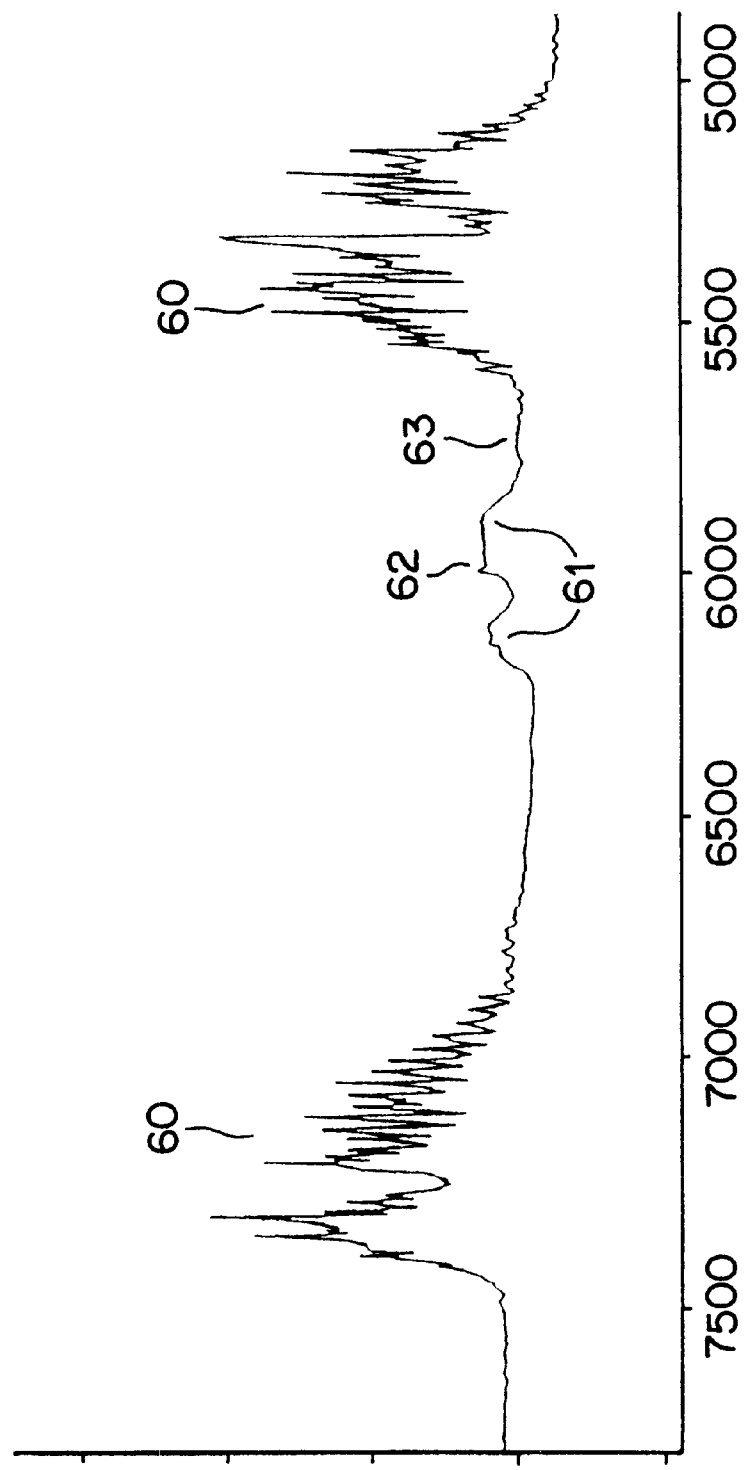
FIG. 3 is-an example of a near infrared spectrum which can be produced using the instant invention.

Referring now to FIG. 3, therein is shown an example of a near infrared spectrum which can be obtained using the instant invention. Peaks 60 represent steam, peak 61 represents alkenes, peak 62 represents aromatic hydrocarbons, and peak 63 represents alkanes. However, the peaks are broad and overlapping, and thus are not as suitable for traditional spectroscopic quantitative analysis as may be desired.

Chemometrical methods such as multivariate calibration can be used in order to establish the concentrations of individual materials when spectra have the characteristics shown in FIG. 3 and discussed above. "Chemometrics is the science of relating measurements made on a chemical system to the state of the system via application of mathematical or statistical methods. The goal of many chemometrics techniques is the production of an empirical model, derived from data, that allows one to estimate one or more properties of a system from measurements." *Process Analytical Chemistry*, 259 (F. McLennan and B. R. Kowalski eds., Chapman & Hall, 1995). Standard chemometrics software packages are available which can be used to analyze the data generated by near infrared spectroscopy. The spectrum shown in FIG. 3 is the average of 256 scans, although more or fewer scans can be averaged. Thus, numerous data points are available for use with the chemometrics software.

EXAMPLE 1

The apparatus described above is placed at point 16 in FIG. 1. Both of the optical wells have diamond windows with gold brazing (Drukker The Netherlands). The windows are 6.5 millimeters in, diameter and have a thickness of 0.25 millimeters.

Both of the optical probes are single fiber transmission probes. One probe is used to send the near infrared light, while the other probe is used to receive the light after it passes through the crack gas. The fibers in the probes are gold-coated/soldered fibers with a diameter of 400 microns (TOP-sensors, part #CB4294). The lenses in the probes are planoconvex lenses made of BK7 glass with a diameter of 5 millimeters. The outer shell of the probe is 316 stainless steel.

Near infrared spectroscopy is conducted using a BOMEM type FT-NIR instrument (BOMEM Model MB160). The instrument is equipped with a cooled InAs-detector module (BOMEM Model D50B). The interfacing of the spectrometer with the fiber optic cables was done via the Universal Fiber Optic Interface SNG29G, manufactured by Bomem.

The spectrum in FIG. 3 results. FIG. 3 is the average of 256 scans and is composed of about 1000 separate data points. CAAP software (Bomem) is used to collect spectra by a Compaq Deskpro XL466 computer. The spectral data is treated using GRAMS/386 and PLS-plus software (Galactic Ind. Corp.). Thus, this chemometrics software uses a partial least squares (PLS) method of regression analysis.

The components of interest include methane, propylene, the methane/propylene ratio (MPR), ethylene, and the propylene/ethylene ratio (PE). Cracking severity is controlled by adjusting the MPR and PE until they are optimized.

What is claimed is:

1. A method for controlling cracking severity in a cracking furnace, the cracking furnace having at least one cracking tube, the cracking tube being heated to a temperature, the cracking tube containing a feed mixture that is fed into the cracking tube and an gaseous effluent that flows from the cracking tube, the feed mixture having a composition and a residence time in the cracking tube, the method comprising the steps of:

(a) determining the near infrared spectrum of the gaseous effluent in-line by shining a beam of near infrared light first through a first protective gas stream, then through the gaseous effluent, and then through a second protective gas stream to a detector; and (b) changing a process variable selected from the group consisting of the temperature of the cracking tube, the composition of the feed mixture and the residence time of the feed mixture in the cracking tube according to the determination of step (a).

2. The method of claim 1, wherein the feed mixture contains a percentage of steam and wherein the process variable changed in step (b) is selected from the group consisting of the temperature of the cracking tube, the residence time of the feed mixture in the cracking tube and the percentage of steam in the feed mixture.

3. The method of claim 1, wherein in step (b) a chemometric treatment is made of the determination of step (a).

4. The method of claim 3, wherein the chemometric treatment is multivariate calibration analysis or partial least squares regression analysis.

* * * * *